United States Patent [19]

Molnar et al.

[11] Patent Number: 4,526,898

[45] Date of Patent: * Jul. 2, 1985

[54] ANTIHYPERTENSIVE 4-(2-IMIDAZOLIN-2-YL-AMINO)-2-METHYL-INDAZOLE

[75] Inventors: Istvan Molnar; Kurt Thiele; Felix Geissmann; Ulrich Jahn, all of Zofingen, Switzerland

[73] Assignee: Siegfried Aktiengesselschaft, Zofingen, Switzerland

[*] Notice: The portion of the term of this patent subsequent to Mar. 13, 2001 has been disclaimed.

[21] Appl. No.: 530,145

[22] Filed: Sep. 7, 1983

Related U.S. Application Data

[63] Continuation-in-part of Ser. No. 375,116, Apr. 28, 1982, Pat. No. 4,436,913.

[51] Int. Cl.$^3$ .................. A61K 31/415; C07D 403/12
[52] U.S. Cl. .................................... 514/392; 548/316
[58] Field of Search ..................... 548/316; 424/273 R

[56] References Cited

U.S. PATENT DOCUMENTS 4,436,913 3/1984 Molnar et al. .................... 548/316

Primary Examiner—Richard A. Schwartz
Attorney, Agent, or Firm—Jordan and Hamburg

[57] ABSTRACT 4-(2-Imidazolin-2-yl-amino)-2-methyl-indazole is a highly selective and effective $\alpha_2$-antagonist, $\alpha_1$-partial agonist and $\alpha_{1s}$-agonist and displays anti-hypertensive activity and antagonistic activity on adrenaline and noradrenaline. It is useful as an $\alpha$-adrenoceptor influencing and as an anti-hypertensively active drug.

3 Claims, No Drawings

ANTIHYPERTENSIVE 4-(2-IMIDAZOLIN-2-YL-AMINO)-2-METHYL-INDAZOLE

CROSS REFERENCE

This application is a continuation-in-part of Ser. No. 06/375,116 filed on Apr. 28, 1982, now U.S. Pat. No. 4,436,913, based on PCT Application PCT/EP 80/00094 filed Sept. 5, 1980.

BACKGROUND OF THE INVENTION

1. Field of the Invention

The present invention relates to a 2H-indazole derivative, more precisely to a 2-methyl-indazole derivative.

2. Description of the Prior Art

Clonidine (INN for 2-((2,6-dichloro-phenyl)-imino)-imidazolidine) and Phenoxybenzamine (INN for N-benzyl-N-(2-chloroethyl)-N-(1-methyl-2-phenoxy-ethyl)-amine) rank amongst the most valuable anti-hypertensives. Both are in use as drugs. Nevertheless, both have significant drawbacks, especially as to side-effects and contra-indications. Clonidine is an $\alpha_2$-agonist, i.e. it has stimulating agonist activity on the prejunctional $\alpha_2$-adrenoceptors, especially those in the medulla oblongata. Clonidine thus penetrates the blood-brain barrier for central anti-hypertensive action.

Phenoxybenzamine in contrast is an $\alpha_2$-adrenoceptor antagonist at higher concentration and a very effective $\alpha_1$-adrenoceptor blocker already at lower concentration. Nevertheless, phenoxybenzamine, too, readily penetrates the blood-brain barrier.

In consequence, regardless of their valuable anti-hypertensive activity, both, clonidine and phenoxybenzamine, show significant side-effects such as a central nervous system depression (sedation, prostration and hyporeactivity) tachycardic reaction and orthostatic regulation disturbance.

Finally, a series of 1H-indazole derivatives is disclosed in the U.S. Pat. Nos. 3,847,934 and 4,036,976. To applicants' best knowledge none of said prior art 1H-indazole derivatives is in commercial use as a drug. The most anti-hypertensively active species out of said 1H-indazoles is the compound 4-(2-imidazolin-2-yl-amino)-1-methyl-indazole as disclosed in U.S. Pat. No. 4,036,976.

Having a therapeutic index $LD_{50}/ED_{50}$ in the range of 400 (nephrogenic GOLDBLATT-hypertensive rats, p.o.) to 800 (genetically fixed hypertension rats, p.o.), the 4-(2-imidazolin-2-yl-amino)-1-methyl-indazole shows an activity and a therapeutic range comparable to the corresponding data for clonidine. However, obviously also the aforementioned 1-methyl-indazole derivative penetrates the blood-brain barrier, and thus causes similar side-effects as discussed above.

THE OBJECTS OF THE INVENTION

It is thus an object of the invention to find an adrenoceptor-active, especially anti-hypertensively active substance that would not cause a clonidine-like sedation and have no influence on the heart-rate and orthostatic regulation.

It is another object of the invention to find an adrenoceptor-active substance that will not readily cross or penetrate the blood-brain barrier and yet will be highly active.

It is still another object of the invention to find an adrenoceptor-active substance having a low toxicity and a high therapeutic range.

SUMMARY OF THE PRESENT INVENTION

For solving the above objects the inventors synthesized the novel compound 4-(2-imidazolin-2-yl-amino)-2-methyl-indazole having the formula

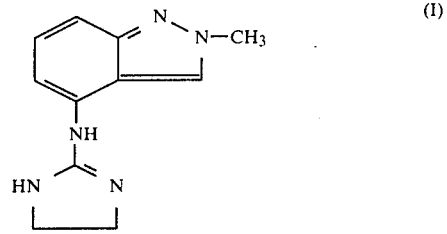

The compound of formula (I) is capable of tautomerism, and its tautomeric form is

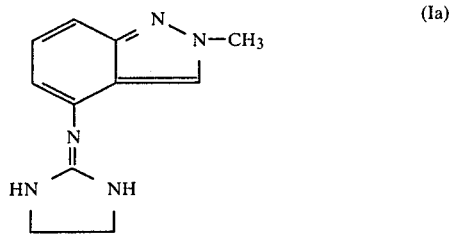

The tautomeric form of 4-(2-imidazolin-2-yl-amino)-2-methyl-indazole having the above formula (Ia) is understood to be also comprised in the present invention. However, for the sake of simplicity reference is made hereafter just to the amino-form of formula (I).

The compound of formulae (I) and (Ia) is a basic substance, and the present invention also includes apart from the free base of formulae (I) and (Ia) its acid addition salt with organic and anorganic acids, especially its pharmaceutically acceptable salt. Suitable inorganic acids for salt formation are nitric acid, hydrohalic acids, sulphuric and phosphoric acid, and suitable organic acids are toluenesulphonic, acetic malonic, succinic malic, melic and tartaric acid. Especially the hydrochloride is of eminent galenic interest.

The compound of the invention is a highly selective and highly specific adrenoceptor-active substance. It is (i) a complete antagonist for $\alpha_2$-adrenoceptors, (ii) a partial agonist for $\alpha_1$-adrenoceptors, (iii) a complete and highly specific agonist for extra-cellular calcium controlled $\alpha_{1s}$-adrenoceptors, and (iv) a highly active adrenaline and noradrenaline antagonist converting the vasopressor effect of said compounds into a depressor response, thus acting anti-hypertensively. Additionally the 4-(2-imidazolin-2-yl-amino)-2-methyl-indazole does not readily penetrate the blood-brain barrier, does not induce drug-metabolising enzymes in the liver, i.e. does not interfere with other drugs, does not cause clonidine-like behavioural changes, and finally has a remarkable low toxicity. 4-(2-imidazolin-2-yl-amino)-2-methyl-indazole thus is a pharmacologically useful compound.

This invention thus further relates to the utilization of the aforementioned substance as an active blood-pressure lowering and adrenoceptor-influencing substance for the manufacture of pharamceuticals for animal and human medicine.

DETAILED DESCRIPTION OF THE INVENTION

The compound of formula (I) can be produced by many different processes.

One method for producing the indazole compounds of formula (I) is characterized in that 4-amino-2-methyl-indazole is condensed with a compound of the formula

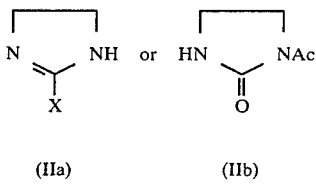

(IIa)  (IIb)

wherein X is a group that is splittable with hydrogen under condensation conditions, preferably a halogen, especially chlorine, and Ac is an acyl group, especially a lower alkyl acyl group or a substituted or unsubstituted phenyl acyl group.

If a compound of formula IIa is used as a starting substance for this condensation, then such substance is preferably introduced in the form of a free base in the presence of a polar or non-polar solvent. Alcohols, ether or chlorinated hydrocarbons serve as solvents. Condensation proceeds in a temperature range between room temperature and about 150° C. The precipitated product, in the form of a salt, is separated and worked up.

When substituent X in formula IIa is an alkylthio-group or a nitroamino group, then the substance of formula IIa is preferably introduced in the form of a salt, condensation in methanol or ethanol proceeding at increased temperature.

When condensation proceeds with a substance of formula IIb, then the process may be especially carried out in a solution or suspension of the amine, preferably POCl$_3$. Condensation proceeds at increased temperature, especially when using POCl$_3$ at temperatures up to the boiling point of the POCl$_3$. The acetyl compound of the end product is obtained herein, which is then converted in acetic acid or methanol into the compound of formula I.

A second method for the manufacture of the substances of formula I is distinguished by in situ formation of the imidazoline ring. In this method, ethylene diamine of the formula H$_2$N—CH$_2$CH$_2$—NH$_2$, as a free base or in the form of a monoacid addition salt is reacted with a 2-methyl substituted indazole, which in the 4-position may either represent a cyanoamino group, or a group

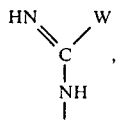

in which W, under condensation conditions, represents a splittable alkylthio group, an alkoxy group, an amino group or nitroamino group, or has a —N=C(Hal)$_2$ group, wherein Hal represents a halogen atom. In the manufacture of the imidazoline derivative by this method, the indazole ring system preferably has at the 4-position an isothiurionium-amino group of the formula

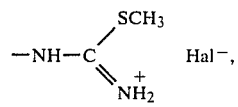

in which the halide is preferable an iodide. When this substituent is especially the isothiuroniumiodidamino group, the ring closure condensation is effected in an inert solvent, for example in methanol or dioxane in a temperature range between about 40° to 210° C. When the substituent in the indazole ring system is a cyano-amino group; the reaction is effected in aliphatic alcohols, ether or aliphatic hydrocarbons at increased temperatures in a range between about 60° to 220° C.

The reaction products obtained by one of these processing variants can be separated in the usual manner and purified by re-crystallization.

According to a third method the compound of formula (I) may be made by subsequently introducing the imidazolin-2-yl-amino group in a way such that the group

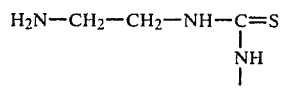

is initially introduced at the 4-position of the indazole ring, wherein the sulfur may also be replaced in this group by an oxygen atom, and on which the ring closure condensation is then effected. The reaction preferably proceeds in a polar solvent, for example dimethyl-formamide, methanol, ethanol or water, at moderately high temperatures in a range from about 30° to 160° C. in the presence of basic substances, such as, for example, alkali metal hydroxide.

The starting substances necessary to execute the preceding methods for manufacture of the substances of the formula I are either available on the market or readily can be produced by methods described in the pertinent technical literature.

DETAILED DESCRIPTION OF PREFERRED EMBODIMENTS OF THE INVENTION

EXAMPLE

Preparation of 4-(2-Imidazolin-2-yl-amino)-2-methyl-indazole hydrochloride

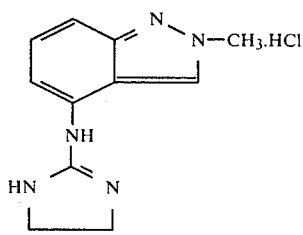

4 g 4-amino-2-methyl-indazole is dissolved in 120 ml THF. The solution is treated with a solution of 2-chloro-imidazoline base, which is prepared from 10 g 2-chloro-imidazoline sulfate (prepared according to J. Heteroc. Chem. 11, 258) with 2n NaOH in methylene chloride.

After three days of standing at 20° C., the hydrochloride product has completely precipitated. The product is filtered and recrystallized from isopropanol. The recrystallized hydrochloride has a melting point from 270° to 271° C., obtained with a yield of 60%.

Hereafter the compound of the invention is called "Sgd 101/75" for short.

ACTIVITY TESTS

Test 1

Activity of Chlonidine and Sgd 101/75 on the Central Nervous System (CNS)

All tests were carried out under identical conditions according to standard testing methods. The animal species used, the route of administering the material to be tested, the type of test and the results obtained are shown in Table I hereunder.

TABLE I

Activity of Sgd 101/75 and clonidine on the CNS

| | | | Effective dose | |
|---|---|---|---|---|
| Species | Route | Test | Clonidine mg/kg | Sgd 101/76 mg/kg |
| Mouse | p.o. | Double hexobarbitone sodium sleeping time | 0.3 | >100 |
| Mouse | p.o. | Double ethanol sleeping time | 0.02 | >100 |
| Rat | p.o. | Double chloralhydrate sleeping time | 0.05 | >100 |
| Mouse | p.o. | 50% reduction in exploratory behaviour | 0.12 | 72 |
| Rat | p.o. | 50% reduction in tetrabenazine-induced ptosis | 0.3 | 33 |
| Mouse | s.c. | 50% reduction of 5HTP-induced head twitches | 0.028 | 28 |
| Mouse | p.o. | 50% inhibition of acetic acid-induced writhing | 0.07 | 4.5 |
| Mouse | p.o. | 50% inhibition of heat-induced tail flick | 5.0 | >100 |
| Chick | i.v. | Dose to induce sleep | 0.01 | >10 |

Further, when conscious cats received clonidine (1 mg/kg i.p.) they exhibited signs of CNS depression (sedation, prostration, hyporeactivity to auditory stimulation, loss of skeletal muscle tone), exophthalmos and piloerection that was marked for 8 h, persisted to a lesser extent for 24 h, and had returned to normal at 48 h. There were no apparent behavioural changes with Sgd 101/75 (4 and 10 mg/kg i.p.).

From the above data it is evident that the compound of the invention (Sgd 101/75) does not cause side-effects which typically are found with clonidine.

Test 2

Sgd 101/75 as an Antagonist for Adrenaline

Experimental hypertension was induced in anaesthetised cats by administering (i.v.) adrenaline. Upon achieving the maximum adrenaline vasopressor effect Sgd 101/75 is administered intraduodenally in an amount of 5 to 10 mg/kg b.w. bringing about within a response time of about 1 to 2 min a conversion of the vasopressor effect of adrenaline into a depressor response, i.e. bringing about an adrenaline reversal.

Test 3

Comparing Sgd 101/75 with 4-(2-imidazolin-2-yl-amino)-1-methyl-indazole of U.S. Pat. No. 4,036,976 ("Sgd 230/75")

Toxicity values were determined applying identical standard methods. The data obtained are listed herebelow in Table II showing $LD_{50}$ values as mg/kg body weight.

TABLE II

| | $LD_{50}$ (mg/kg) | | | |
|---|---|---|---|---|
| | Mouse | | Rat | |
| | i.v. | p.o. | i.v. | p.o. |
| Sgd 101/75 | 58 | 3900 | 69 | 3220 |
| Sgd 230/75 | 22 | 600 | 90 | 1200 |

The results listed in Table II clearly show a significantly higher $LD_{50}$, i.e. a considerable lower toxicity of Sgd 101/75 if compared with its art isomer Sgd 230/75.

Test 4

Comparing anti-hypertensive activity and therapeutic range of Sgd 101/75 and Sgd 230/75

Antihypertensive activities for Sgd 101/75 of the invention and Sgd 230/75 of U.S. Pat. No. 4,036,976 were determined with nephrogenic GOLDBLATT hypertensive rats.

The $ED_{50}$ values obtained p.o. were 4.2 mg/kg for Sgd 101/75 and 3.0 mg/kg for Sgd 230/75. The antihypertensive activity of the compound of the invention thus runs to about 190% of the activity of the prior art compound, taking into account the respective $LD_{50}$ values (rat, p.o) of 3220 and 1200 mg/kg, respectively, the therapeutic index $LD_{50}/ED_{50}$ is 767 and 400 for the compound of the invention and of the art, respectively.

When used as a drug for the larger mammal or humans the compound of the invention preferably is administered in a total daily dosage in the range from about 0.4 to about 50 mg depending on the mode of administering and the therapy desired. The total daily dosage can but need not be administered in two or three equal weight portions. Oral administration is preferred. The active compound of the invention is formulated in association with a common inert diluent or carrier material in liquid or solid state. Other common active compounds may be also contained in the final dosage form, as to need, especially since no interference is to be feared from the presence of the compound of the invention.

What we claim is:

1. The compound 4-(2-imidazolin-2-yl-amino)-2-methyl-indazole or an acid addition salt thereof.

2. A pharmaceutical composition useful in selectively acting on α-adrenoceptors in mammals and humans comprising a therapeutically effective amount of a compound of claim 1 associated with a common liquid or solid diluent or carrier material.

3. A pharmaceutical composition useful in treating hypertension comprising a therapeutically effective amount of a compound of claim 1 associated with a common liquid or solid diluent or carrier material.

* * * * *